United States Patent [19]

D'Alo et al.

[11] Patent Number: 4,888,008
[45] Date of Patent: Dec. 19, 1989

[54] VENTED SPIKE CONNECTION COMPONENT

[75] Inventors: Herbert F. D'Alo, Madison; Christine D. Enger, Milford, both of Conn.

[73] Assignee: Sherwood Medical Company, St. Louis, Mo.

[21] Appl. No.: 239,044

[22] Filed: Aug. 30, 1988

Related U.S. Application Data

[63] Continuation of Ser. No. 21,181, Mar. 3, 1987, abandoned.

[51] Int. Cl.⁴ ............................................. A61B 19/00
[52] U.S. Cl. .................................................. 604/411
[58] Field of Search ................ 604/411, 405, 251–256, 604/266, 249, 247

[56] References Cited

U.S. PATENT DOCUMENTS

| | | |
|---|---|---|
| 2,409,343 | 10/1946 | Curtis . |
| 2,668,533 | 2/1954 | Evans .................................. 604/405 |
| 2,817,372 | 12/1957 | Barr et al. . |
| 2,852,024 | 9/1958 | Ryan ................................... 604/251 |
| 3,507,395 | 4/1970 | Bently ................................. 604/122 |
| 3,542,240 | 11/1970 | Solowey .............................. 604/411 |
| 4,332,247 | 6/1982 | Mittleman et al. ................. 604/122 |
| 4,505,709 | 3/1985 | Froning ............................... 604/411 |
| 4,534,758 | 8/1985 | Akers et al. ........................ 604/411 |
| 4,588,403 | 5/1986 | Weiss et al. ........................ 604/411 |

FOREIGN PATENT DOCUMENTS

| | | |
|---|---|---|
| 245223 | 10/1946 | France . |
| 1256419 | 4/1970 | United Kingdom . |
| 2171678 | 9/1986 | United Kingdom . |

*Primary Examiner*—John D. Yasko
*Attorney, Agent, or Firm*—Andrew J. Beck; Montgomery W. Smith; Richard D. Allison

[57] ABSTRACT

A connection component suitable for use with an enteral fluid delivery set is arranged in the form of a replacement for the cap of a pre-filled, foil sealed fluid container. The connection component includes a fluid outlet passage which is arranged in the form of a projecting spike which penetrates and opens the foil seal as the connection component is attached to the pre-filled container.

16 Claims, 1 Drawing Sheet

VENTED SPIKE CONNECTION COMPONENT

This application is a continuation of application Ser. No. 021,181, filed on Mar. 3, 1987, now abandoned.

BACKGROUND AND SUMMARY OF THE INVENTION

The present invention relates to a connection component arranged for mounting on a tubing assembly for connection to a prefilled, foil-sealed container, and in particular to a connection component which includes a spike for penetrating a foil seal and an air vent.

In an enteral fluid delivery system for a patient, there is a need to provide a component that will effect a quick connection of a fluid delivery set to a prefilled, foil-sealed container containing enteral nutritional fluid. In such systems the connecting component is preferrably in the form of a cap, which replaces the shipping cap on the prefilled container, and includes means for perforating the foil seal on the container during attachment. Such automatic perforation is desirable to simplify the set-up procedure. It is further desirable that the connecting component provide a means to allow air to vent into the container as fluid flows from the container. Such venting should be achieved without permitting venting air bubbles from entering the outlet flow channel.

Accordingly, it is an object of the present invention to provide a connection component for effecting a quick coupling between a fluid delivery set and a prefilled, sealed container that minimizes the time of exposure of the container contents between seal puncture and attachment to the fluid delivery set.

Another object of this invention is to provide such a connection component for use with prefilled, foil-sealed containers that inhibits entry of air into the fluid flow path.

A still further object of this invention is to provide such a connection component that can puncture and deform the seal of a prefilled bottle in a manner that permits the venting of air into the container and the pumping of fluid therefrom.

These and other objects of the invention are obtained by means of a connection component adapted to be attached to a prefilled, fluid container, said component including a circular wall portion, a pointed projecting member extending from the wall portion and spaced from the center of the wall portion, said projecting member having a fluid receiving passage passing through the wall portion, said projecting member being spaced from the center of the wall portion, and an air vent on the wall portion, spaced from the center of the wall portion at a position opposite from said projecting member.

For a better understanding of the invention, as well as other objects and further features thereof, reference is had to the following detailed description of the preferred embodiments which makes reference to the following set of drawings.

DETAILED DESCRIPTION OF THE PREFERRED EMBODIMENTS

Figure 1:
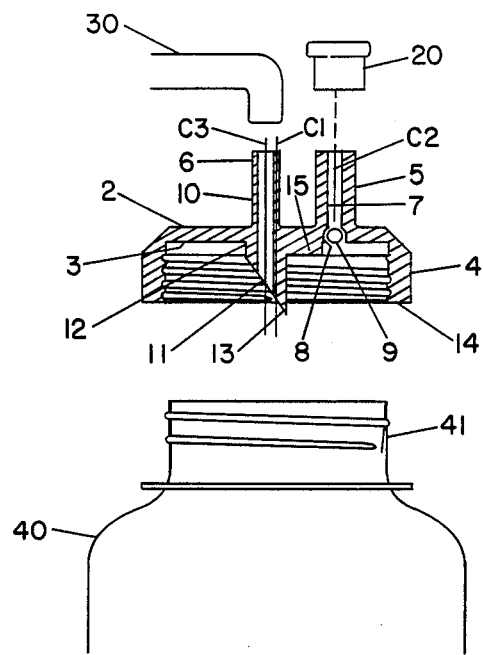
FIG. 1 is a perspective assembly view, partly in section along the line 1—1 of FIG. 2, of a connection component according to the present invention.
Figure 2:
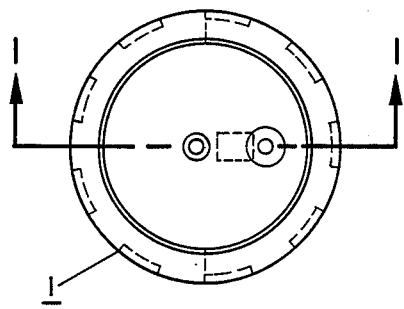
FIG. 2 is a top view of the connection component shown in FIG. 1.

Referring to FIGS. 1 and 2 the vented spike connection component of the present invention is generally comprised of a housing body 1 including a circular wall having a top surface 2, a bottom innerside surface 3, and a rim 4 adapted to be detachably mounted to the neck 41 of a prefilled container 40. The connection component is preferably formed from molded plastic and has a one piece construction.

The housing body 1 is provided with two cylindrically shaped members 5 and 6 extending outward from surface 2. Member 5 has an internal passage of which forms an air vent and includes a one way valve 9 arranged within recess 8 formed as an enlargement of the inner end of passage 7. A cover 20 may be provided to close passage 7 prior to use.

Cylindrical member 6 includes a top portion 10 extending outward from surface 2 and is adapted to be attached to a plastic tubing 30 which along with the connection component forms an enteral fluid delivery set. Cylindrical member 6 also includes a bottom portion 11 having a spike formed by truncating the cylindrical member portion 11 with an intersecting angled plane starting at a location 12 just below the bottom surface 3 of the housing body 1 to a point 13 extending below the edge 14 of the rim 4. Member 6 includes a central passage through which enteral fluid can pass from container 40 into tubing 30.

In the FIG. 1 embodiment, the circular wall formed between surfaces 2 and 3 has a central axis designated C1 about which the connection component is rotated for attachment to fluid container bottle 40. In the illustrated embodiment cylindrical member 5 and 6 are each offset from axis C1 on opposite sides of C1. In addition the shape of the spike 13 formed on portion 11 of cylindrical member 6 is oriented so that the opening of the central passage is facing away from the vent passage 7 formed through member 5. The center C3 of member 6 is offset by approximately 0.1 inch from the center C1 of the connection component. This offset provides for effective action of the spike end 13 in opening a passage through a foil seal on a fluid container 40.

The center C3 of member 6 is offset by approximately 0.5 inch from the center C2 of member 5. This separation, along with the orientation of the opening of the passage in member 6 prevents air bubbles which enter fluid via vent passage 7 from being drawn into the outlet passage in member 6. Additionally, a rib 15 is provided on the bottom innerside surface 3 of the connection component. The rib 15 acts to deflect the seal after it has been punctured, thereby prohibiting the seal from obstructing the air passage in member 5.

Figure 3:
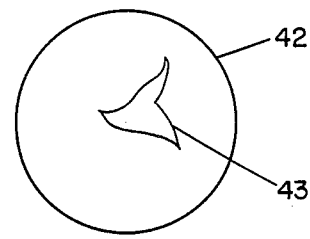
FIG. 3 is a top view of a foil seal of a prefilled container after the seal has been deformed by the attachment of the FIG. 1 connection component to said container.
Figure 4:
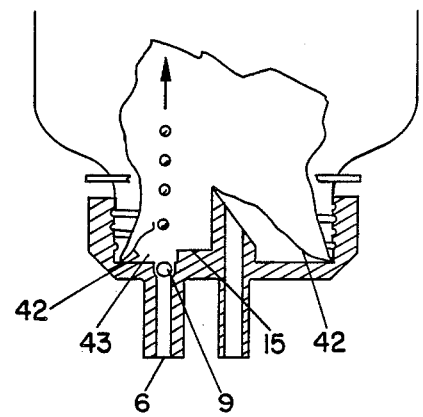
FIG. 4 is a cut-away view after the connection component has been attached to the container as in FIG. 5.

With the aforedescribed vented spike connection component of the present invention, possible interference caused by collection of the seal of the container around the base of the projecting member, after it has pierced the seal of the container, is eliminated by the deformation of the seal in a manner as shown in FIG. 3. This irregularly shaped aperture 43 in the seal 42 is caused by the offset of its centerline C3 of cylindrical member 6 from the axis C1 of the housing. With reference to FIG. 4, the aperture 43 is sufficiently extended to permit air to be vented into the container without being obstructed by the foil seal 42. Also the aperture is sufficiently deformed at the center as to allow clear passage of the fluid to the fluid carrying projecting member 6.

Figure 5:
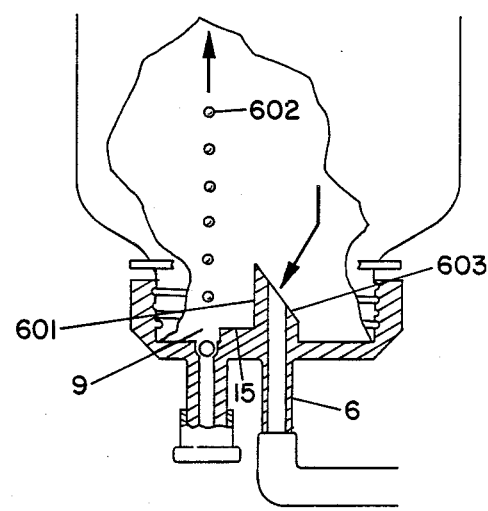
FIG. 5 is a perspective assembly view, partly in section, of the FIG. 1 connection component in operative engagement with a prefilled container.

When in use the connection component according to the present invention disposes the long side 601 of the fluid carrying projecting member 6 adjacent the vented air stream 602 as illustrated in FIG. 5. This placement provides a physical barrier between the vented air stream 602 and the area adjacent the point of fluid exit 603. Coupled with a sufficient distance displacement between the air stream 602 and the fluid exit point 603 they form a system that provides reliable delivery of the fluid from the container to the fluid flow circuit without inducement of air into the circuit in the form of a bubble. Further, the flow of fluid or vent air is not obstructed by the foil seal.

The detailed description of the preferred embodiment of the invention having been set forth herein for the purpose of explaining the principles thereof, it is known that there may be modification, variation or change in the invention without departing from the proper scope of the invention and the claims thereto.

We claim:

1. A connection component for connection to a fluid containing bottle having an opening and a threaded connection for receiving a closure cap, comprising:
   a cap shaped component body including a circular wall portion and a cylindrical threaded portion extending in one axial direction therefrom;
   a pointed projecting member extending from said wall portion spaced from the center of said wall portion on the same side as said threaded portion, said projecting member having a fluid receiving passage passing through said wall portion and having a fluid receiving opening on the side of said projecting member facing away from said center;
   and an air vent on said wall portion spaced from said center in a position opposite said projecting member.

2. A connecting component as specified in claim 1 wherein said projecting member is cylindrical and has a pointed end formed by an intersecting angled plane.

3. A connecting component as specified in claim 1 wherein said projecting member is spaced from said center by at least approximately one tenth of an inch.

4. A connecting component as specified in claim 1 wherein said projecting member is spaced from said air vent by approximately one half of an inch.

5. A connecting component as specified in claim 1 wherein said air vent includes a one-way valve.

6. A connecting component as specified in claim 1 further comprising a rib member displaced on said wall portion between said projecting member and said air vent.

7. A connecting component arranged for attachment to the opening of a fluid container, said connecting component including a wall for covering said opening, a pointed projecting member extending from said wall toward the container at a position spaced from the center thereof, a fluid channel passing through said wall and said projecting member and having a flud receiving opening adjacent the end of said projecting member, the fluid receiving opening spaced from said wall, and an air vent in said wall spaced laterally away from said projecting member on the laterally opposite side of said wall center.

8. A connection component for connection to a fluid containing bottle having an opening, a piercable protective seal covering the opening and a threaded connection for receiving a closure cap, said component comprising:
   a cap shaped component body including a circular wall portion and a cylindrical threaded portion extending in one axial direction therefrom, said threaded portion adapted to threadedly receive the threaded connection on the bottle;
   a pointed projecting member extending from said wall portion, said member having a centerline laterally offset from the centerline of said wall portion on the same side as said threaded portion, said projecting member having a fluid receiving passage passing through said wall portion and having a fluid receiving opening adjacent the end of said projecting member, the fluid receiving opening spaced from said wall portion, said projecting member being cylindrical and said end being pointed such that said pointed end pierces the seal of the bottle to form an aperture in the seal larger than the diameter of said projecting member upon threaded connection of said connection component to said bottle; and an air vent in said wall portion spaced laterally from the center line of said wall portion on a side latrally opposite to said projecting member.

9. The connection component as claimed in claim 8, wherein said pointed end extends further toward said container than any portion of said fluid receiving opening and said pointed end is disposed between said fluid receiving opening and said vent opening.

10. The connection component as claimed in claim 9, wherein all of said fluid receiving opening extends substantially further toward said container than any portion of said vent opening.

11. A connection component arranged for attachment to the opening of a fluid container, said connecting component including a wall for covering said opening, a pointed projecting member extending from said wall toward the container, a fluid channel passing through said wall and said projecting member and having a fluid receiving opening adjacent the end of said projecting member, and a vent passage passing through said wall and having a vent opening, at least a portion of said fluid receiving opening extending further toward said container than any portion of said vent opening and said vent opening being laterally spaced away from said projecting member and on the laterally opposite side of said projecting member from said fluid receiving opening.

12. The connection component as claimed in claim 9, wherein said pointed end extends further toward said container than any portion of said fluid receiving opening and said pointed end is disposed between said fluid receiving opening and said vent opening.

13. The connection component as claimed in claim 12, wherein all of said fluid receiving opening extends substantially further toward said container than any portion of said vent opening.

14. A connection component arranged for attachment to the opening of a fluid container, said connecting component including a wall for covering said opening, a pointed projecting member extending from said wall toward said container, a fluid channel passing through said wall and said projecting member and having a fluid receiving opening adjacent the end of said projecting member, and a vent passage passing through said wall and having a vent opening spaced laterally away from said projecting member on the laterally opposite side of the center of said wall, a portion of said projecting member extending further toward said container than any portion of the fluid receiving opening and being laterally disposed between said fluid receiving opening and said vent opening.

15. The connection component as claimed in claim 14, wherein all of said fluid receiving opening extends substantially further towad said container than any portion of said vent opening.

16. The connecting component claimed in claim 15, wherein said vent opening is recessed from the portion of said wall between said projecting member and said vent opening.

* * * * *